United States Patent [19]

Suzuki et al.

[11] 4,422,978
[45] Dec. 27, 1983

[54] METHOD FOR PREPARING OPTICALLY ACTIVE CARBOXYLIC ACID ESTERS

[75] Inventors: Yukio Suzuki; Masahiro Hayashi, both of Toyonaka; Kenzi Takuma, Nara, all of Japan

[73] Assignee: Sumitomo Chemical Company, Limited, Osaka, Japan

[21] Appl. No.: 313,089

[22] Filed: Oct. 20, 1981

[30] Foreign Application Priority Data

Oct. 20, 1980 [JP] Japan .................................. 55-147265
Apr. 15, 1981 [JP] Japan .................................. 56-56115

[51] Int. Cl.³ ............................................ C07C 121/75
[52] U.S. Cl. ................................................. 260/465 D
[58] Field of Search ..................................... 260/465 D

[56] References Cited

U.S. PATENT DOCUMENTS

| | | | |
|---|---|---|---|
| 4,176,195 | 11/1979 | Stoutamire | 424/304 |
| 4,238,406 | 12/1980 | Suzuki et al. | 260/465 D |
| 4,279,924 | 7/1981 | Suzuki et al. | 424/304 |
| 4,293,504 | 10/1981 | Suzuki et al. | 260/465 D |
| 4,312,816 | 1/1982 | Oketa et al. | 260/465 D |
| 4,321,212 | 3/1982 | Suzuki et al. | 260/465 D |

Primary Examiner—Dolph H. Torrence
Attorney, Agent, or Firm—Sughrue, Mion, Zinn, Macpeak and Seas

[57] ABSTRACT

A method for preparing an optically active carboxylic acid ester of the formula (I):

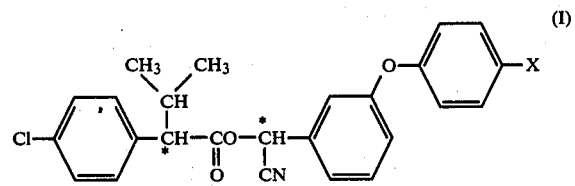

wherein X is a hydrogen atom or a fluorine atom, and * indicates an asymmetric carbon atom, which is an Aα-isomer having an (S)-configuration on both the acid and alcohol moieties, or rich in said Aα-isomer, which method comprises crystallizing said Aα-isomer from a solution of an A-isomer of the formula (I) having an (S)-configuration on the acid moiety in the presence of a crystal that is of substantially pure Aα-isomer and in the presence or absence of a basic catalyst.

59 Claims, 2 Drawing Figures

METHOD FOR PREPARING OPTICALLY ACTIVE CARBOXYLIC ACID ESTERS

This invention relates to a method for preparing an isomer of the formula (I):

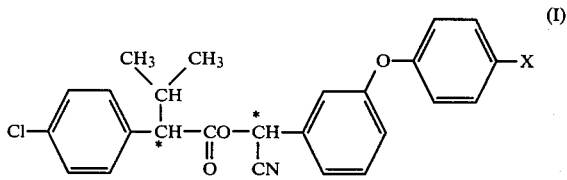

wherein X is a hydrogen atom or a fluorine atom, and * indicates an asymmetric carbon atom, which has been an (S)-configuration on both the acid and alcohol moieties, as well as a mixture rich in such isomer.

α-Cyano-3-phenoxybenzyl-2-(4-chlorophenyl)-isovalerate (hereinafter, this command being referred to as "fenvalerate") and α-cyano-3-(4-fluorophenoxy)-benzyl-2-(4-chlorophenyl)isovalerate (hereinafter, this compound being referred to as "p-F fenvalerate") are useful as insecticides and/or acaricides as disclosed in, for example, Japanese patent application (OPI) No. 26425/74 (U.S. Pat. No. 4,062,968) and Japanese patent application (OPI) No. 125145/77 (British Pat. No. 1,549,462) (the term "OPI" as used herein refers to a "published unexamined Japanese patent application"). These esters have one asymmetric carbon atom on each of the acid and alcohol moieties, and therefor, four stereoisomers are available for each ester.

These stereoisomers are hereunder referred to as shown in Table 1 below.

TABLE 1

| | Abbreviations for Stereoisomers | | |
| --- | --- | --- | --- |
| | | Acid Moiety | |
| Alcohol Moiety | (S)-Configuration | Racemic | (R)-Configuration |
| (S)-Configuration | Aα-Isomer | α-Isomer | Bα-Isomer |
| Racemic | A-Isomer | "Racemate" | B-Isomer |
| (R)-Configuration | Aβ-Isomer | β-Isomer | Bβ-Isomer |

Mixtures of isomers rich in Aα-isomers and Aβ- isomers are referred to as Aα-rich and Aβ-rich isomers, respectively.

The A- and Aα-isomers of carboxylic acid ester of the formula (I) are known to have insecticidal and/or acaricidal efficacy about twice and four times as high as that of the racemate, respectively (see Japanese patent application (OPI) Nos. 24019/78 (British Pat. No. 1,560,303) and 104249/80 (GB 2,041,365 A)). The Aα-isomer can be selectively crystallized from the A-isomer by known methods which are described in Japanese patent application (OPI) Nos. 16444/79 (GB Pat. No. 2,001,964 A), 55546/79 (GB Pat. No. 2,001,964 A), 59248/79 (EP 2289), 109945/79 (GB Pat. No. 2,014,137 A) and 104249/80 (GB Pat. No. 2,041,365 A). These methods are advantageous in that once the A-isomer is obtained, it can be converted to the Aα-isomer by a very simple step.

When we tried to obtain the Aα-isomer of fenvalerate from the A-isomer by these methods, we sometimes failed to attain the intended object, and as a result of various studies on the failures, we unexpectedly found that the A-isomer, which is a mixture of the Aα- and Aβ-isomers, forms crystals as a mixture having a ratio of Aα-isomer to Aβ-isomer of substantially 1:1, which crystals have a melting point of 48.5 to 49.5° C., and further that an Aα-isomer of p-F fenvalerate also crystallizes (melting point: 52.0° to 55.5° C.).

As a result of further studies, we found that the presence of a substantially pure crystal of the Aα-isomer in the crystallization system, i.e., the substantial absence of a crystallizing nucleus of the A-isomer, makes it possible to crystallize the Aα-isomer from a solution of the A-isomer with good reproducibility. If the crystals of A-isomer and Aα-isomer are substantially absent in the solution of A-isomer, the supersaturated state of the solution can be maintained relatively stably even if it is under such conditions that the A- or Aα-isomer could be crystallized from the viewpoint of solubility, and the presence of a crystal of only the Aα-isomer in that supersaturated state makes it possible to crystallize the Aα-isomer without the A-isomer being crystallized.

As a result of our continued studies, we also found that when the method described above is carried out on an industrial scale, crystallization of the A-isomer may occur almost spontaneously because iron rust and other inevitable physical stimulants upset the stable supersaturated state of the solution of the A-isomer. We therefore made efforts to develop a method that is capable of consistant crystallization of the Aα-isomer in the presence of such physical stimulants. We consequently discovered that the region of a temperature versus concentration of A-isomer profile in which the supersaturated state of the solution of A-isomer is maintained stable can be predetermined by a method described hereunder, and that the Aα-isomer can be crystallized from the solution of A-isomer consistently within that region. The present invention has been accomplished in consequence of our further studies based on this finding.

In the two Figures, the abscissa represents the concentration (wt%) of A-isomer and the ordinate the temperature (°C.).

One method to eliminate the crystallizing nucleus of A-isomer from the crystallization system is to heat the system to at least 40° C., usually to a temperature higher than the melting point of the A-isomer. Preferably, the system is refluxed using a solvent having a boiling point higher than the melting point of the A-isomer.

Figure 1:
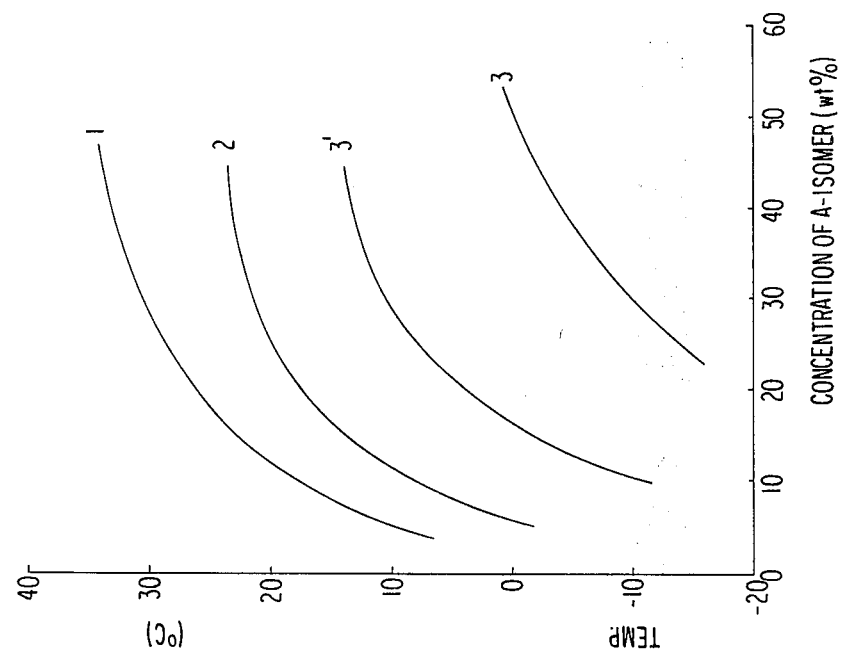
FIG. 1 is a schematic representation of the region of a temperature versus concentration of A-isomer profile in which the supersaturated state of the solution of A-isomer is maintained stable.

The region of a temperature versus concentration of A-isomer in which the supersaturated state of the solution of A-isomer is maintained stable, as well as the method for its determination are hereunder described by reference to FIG. 1. In FIG. 1, curve ① represents a solubility of the crystal of A-isomer with respect to the solvent used. Curve ② represents threshold values of the dissolution of the crystal of Aα-isomer in the solution of A-isomer, this curve being obtained by heating a solution containing a certain concentration of A-isomer, holding the solution at a predetermined temperature, adding the crystal of Aα-isomer to the solution, and checking whether the crystal of Aα-isomer is dissolved. Curve ③ represents threshold values of the crystallization of the A-isomer, which is obtained by heating a solution of a certain concentration of A-isomer containing substances that upset the supersaturated state of the solution such as iron rust, iron powder, glass dust and glass beads, holding the solution at a predetermined temperature for at least 24 hours under stirring, and checking whether the A-isomer is crystallized. Curve ③' represents threshold values of the crystallization of the A-isomer, which is obtained by heating a solution containing a certain concentration of the A-isomer, holding the solution at a predetermined temperature, adding one of the above-mentioned substances that upset the supersaturated state of the solution, holding the resulting solution at a predetermined temperature for at least 24 hours under stirring, and checking whether the crystallization of the A-isomer takes place.

FIG. 1 depicts the relation of the four curves that is observed generally. Curves ③ and ③' may overlap each other, but generally, curve ③' is above curve ③ as shown in the FIGURE. The region above curve ① is a stable area where the crystals of A-isomer and Aα-isomer are dissolved; the region surrounded by curves ① and ② is an area where the crystal of Aα-isomer is dissolved but in the presence of the crystal of A-isomer, the A-isomer is crystallized. The region below curve ③ is an instable area where the A-isomer is crystallized by physical stimulation. The region of a temperature versus concentration of A-isomer profile where the supersaturated state of the solution of A-isomer is maintained stable, namely the region where the crystallization of Aα-isomer from the solution of A-isomer can be carried out with good reproducibility is the area surrounded by curves ② and ③, preferably by curves ② and ③'.

As the physical stimulants or the substances that upset the supersaturated state as referred to in this invention, there can be exemplified solids that can exist in the solution of A-isomer such as metal powders (e.g., iron powder) or rust from them, glass dust, common salt and polymer dust. Other stimulations include radiation, mechanical impacts, thermal stimulation with substances of extremely high or low temperatures, and stimulation with liquid drops insoluble in the solution of A-isomer. Curve ③ or ③' can be conveniently determined with iron rust, iron powder, glass dust, etc.

In this invention, the crystallization of the Aα-isomer from the solution of A-isomer is carried out preferably within the range surrounded by curves ② and ③, more preferably by curves ② and ③', and the supersaturated state of the solution is held stable within this range even if there is a physical stimulant in the solution. The presence of a substantially pure crystal of Aα-isomer in the range surrounded by curves ② and ③, preferably by curves ② and ③', i.e., the substantial absence of the crystal of A-isomer, makes it possible to crystallize the Aα-isomer from the solution of A-isomer with quite good reproducibility. In this method, the Aα-isomer can be crystallized from the solution of A-isomer in a higher yield by reducing the crystallization temperature gradually as the Aα-isomer is crystallized.

Examples of the solvent which can be used for the crystallization of Aα-isomer from the solution of A-isomer are alcohols, aliphatic hydrocarbons, alicyclic hyrdrocarbons and mixed solvents thereof. Mixed solvents consisting of these solvents and aromatic hydrocarbons, ketones, esters, ethers, chlorinated hydrocarbon solvents and phenols can be used. Preferred examples are alcohols alone or in admixture with aliphatic hydrocarbons and/or aromatic hydrocarbons. Preferred alcohols are those having 1 to 5 carbon atoms, such as methanol, ethanol, n-propanol, isopropanol and n-butanol. Preferred aliphatic and alicyclic hydrocarbons are those having 5 to 12 carbon atoms, such as hexane, heptane, octane, petroleum ether, ligroin and methylcyclohexane. Examples of the aromatic hydrocarbons are benzene, toluene and xylene. If the crystallization system contains no basic catalyst, acetic acid or the like can be added in a small amount, say, less than 5% of the solvent. By adding acetic acid or the like, the stability of the supersaturated state of the solution can be increased, and the decomposition of the starting material in the solvent can be prevented. The optimum amount of the solvent used varies with the type and the crystallization temperature, and therefore, cannot be unequivocally defined. But, generally the solvent is used in a weight about 0.5 to 30 times as great as that of the A-isomer.

The use of a basic catalyst is not essential to the purposes of this invention. When the crystallization and isolation of the Aα-isomer has been performed in the absence of a basic catalyst, the ester is recovered from the mother liquor, and the residual ester in the mother liquor which is rich in the Aβ-isomer is brought into contact with a basic catalyst to subject to epimerization on the alcohol moiety to restore the ratio of the Aα-isomer to Aβ-isomer to an equilibrium, and thereafter, the crystallization is again carried out whereby the A-isomer can be converted to the Aα-isomer almost quantitatively. Crystallization and isolation of the Aα-isomer can also be performed in the presence of a basic catalyst, and the advantage of this method is that the crystal of Aα-isomer can be obtained in an amount greater than that of the Aα-isomer initially contained in the A-isomer (usually about 50%). The ester in he mother liquid is recovered and put to further use after purification, if desired.

Alternatively, after the Aα-isomer has been crystallized from the solution of A-isomer in the presence of a basic catalyst, the basic catalyst may be removed or made inert (neutralized) without separating the crystal of Aα-isomer from the mother liquor, and not only the crystal of Aα-isomer but also the A-isomer in the mother liquor is recovered by concentrating all the mother liquor or by other means, whereby an A-isomer rich in the Aα-isomer can be obtained. In this case, the residual Aα-isomer in the mother liquor can be used effectively without being lost. The simplicity of this procedure makes it an economically advantageous method that is adapted to industrial production of the desired isomer.

Examples of the basic catalyst which can be used for the crystallization include nitrogen-containing bases such as ammonia, hydrazine, methylamine, ethylamine, n-propylamine, isopropylamine, n-butylamine, dimethylamine, diethylamine, di-n-propylamine, di-n-butylamine, trimethylamine, triethylamine, cyclohexylamine, ethylenediamine, ethanolamine, pyrrolidine, piperidine, morpholine, aniline, 1-naphthylamine, pyridine, quinoline and 1,5-diazabicyclo[4,3,0]-non-5-ene; phosphorus-containing bases such as triphenylphosphine and tri-n-butylphosphine; quaternary ammonium hydroxides such as tetramethylammonium hydroxide and tetra-n-butylammonium hydroxide; and metal-containing bases such as sodium hydroxide, potassium hydroxide, sodium carbonate, sodium cyanide, sodium methylate, sodium hydride and sodium amide, with the ammonia and triethylamine being preferred. The amount of the basic catalyst used varies with the type of the catalyst and solvent, their amount and the crystallization temperature, but it is used generally in an amount of 0.001 to 200 mol% per mol of the starting ester, and ammonia and triethylamine are desirably used in an amount of 5 to 100 mol% per mol of the starting ester.

The seed crystal of Aα-isomer must be substantially free of the crystal of A-isomer, but the generally obtained crystalline Aα-isomer or Aα-rich isomer contains the Aβ-isomer, and there is the possibility that the crystal of A-isomer is formed. Therefore, it is preferred that such crystal be used after one or more recrystallizations. The crystal of Aα-isomer obtained by recrystallization may be not isolated but mixed with the solution of A-isomer as a seed crystal together with the mother liquor. The solvent used for recrystallization may be the same as or different from the solvent used for the crystallization of the Aα-isomer from the solution of A-isomer. Examples of the solvent which can be used for the recrystallization are alcohols, aliphatic or alicyclic hydrocarbons or mixtures thereof. These solvents may also be mixed with aromatic hydrocarbons, ketones, esters, ethers, chlorinated hydrocarbon solvents and phenols. Preferred examples are alcohols which are used alone or in combination with aliphatic hydrocarbons and/or aromatic hydrocarbons, as well as aliphatic hydrocarbons used alone or in combination with aromatic hydrocarbons. Preferred alcohols are those having 1 to 5 carbon atoms, such as methanol, ethanol, n-propaol, isopropanol and n-butanol. Preferred aliphatic or alicyclic hydrocarbons are those having 5 to 12 carbon atoms, such as hexane, heptane, octane, petroleum ether, ligroin and methylcyclohexane. Prefered aromatic hydrocarbons are benzene, toluene and xylene. The optimum amount of the solvent varies with the type of solvent, but generally, it is used in a weight of 0.5 to 50 times, preferably at least 3 times, as great as that of the Aα-isomer. To prevent the denaturation or deterioration of the Aα-isomer, a small amount (e.g., less than 5% of the solvent) of acetic acid may be added to the solvent.

The crystallization of the Aα-isomer from A-isomer is generally conducted at a temperture of 25° C. or less, preferably between −30 and 20° C.

This invention is now described in greater detail by reference to the following examples, reference examples and comparative examples which are give here for illustrative purposes only and are by no means intended to limit its scope.

COMPARATIVE EXAMPLE I

Forty grams of a liquid A-isomer of fenvalerate (optical purity on the acid moiety : 94.2%, Aα/Aβ=49.5/50.5) was dissolved in 46.8 g of heptane and 5.2 g of toluene under heating, and then cooled to 25° C. After addition of 28 g of methanol, the mixture was cooled to −16° C., and 1 mg of a crystal of an Aα-isomer of fenvalerate (optical purity on the acid moiety: 99.2%, Aα/Aβ=97.7/2.3) and 7.2 cc of 8.4% ammonia in methanol were added thereto, and the resulting mixture was left to stand under stirring at the same temperature. One hour after the stirring, the mixture started to crystallize abruptly. Two hours later, 2.2 cc of acetic acid was added to the mixture which was then filtered to give 33.27 g of a crystalline isomer mixture of fenvalerate whose Aα/Aβ ratio was 47.5/52.5.

REFERENCE EXAMPLE 1

A hundred grams of the crystal of Aα-isomer of fenvalerate used as a seed crystal in Comparative Example 1 was dissolved in 233 cc of heptane and 33 cc of toluene at 34° C. The solution was cooled to 20° C. and seeded with 1 mg of the same crystal and cooled to 7° C. over one hour and stirred for 1.5 hours at that temperature. The mixture was filtered to give 81.67 g of a crystal. Fifty grams of the crystal was recrystallized in the same manner as above to give 41.68 g of a crystal of Aα-isomer of fenvalerate (Aα/Aβ=99.9/0.1, optical purity on the acid moiety: 100.0%).

COMPARATIVE EXAMPLE 2

The procedure of Comparative Example 1 was repeated except that 4 g of the crystal of Aα-isomer of fenvalerate obtained in Reference Example 1 and 0.1 mg of the crystal of A-isomer of fenvalerate were used as seed crystals. One day later, 2.2 cc of acetic acid was added to the mixture, and the resulting crystal was filtered to give 38.02 g of a crystal of A-isomer of fenvalerate having an Aα/Aβ ratio of 48.7/51.3.

COMPARATIVE EXAMPLE 3

The procedure of Comparative Example 1 was repeated except that the 8.4% ammonia in methanol was not used. Three hours later, the resulting crystal was filtered to give 30.74 g of a crystal of fenvalerate having an Aα/Aβ ratio of 49.1/50.9.

EXAMPLE 1

Forty grams of an A-isomer of fenvalerate which was the same as used in Comparative Example 1 except that all of it was crystallized was dissolved in 46.8 g of heptane and 5.34 g of toluene under heating. The solution was cooled to room temperature (i.e., about 20° to 30° C.) at which temperature 28 g of methanol was added. Then, the mixture was cooled to −16° C., and 1 mg of the Aα-isomer of fenvalerate obtained by recrystallization in Reference Example 1 and 7.2 cc of 8.4% ammonia in methanol were added thereto. The resulting mixture was stirred at −16° C. for one day and mixed with 15 cc of 10% hydrochloric acid, 50 cc of water and 20 cc of toluene. After stirring the mixture at room temperature, the aqueous layer was separated, and the oily layer was washed with water twice. The oily layer was concentrated to give 39.87 g of an Aα-rich isomer of fenvalerate (Aα/Aβ=92.2/7.8).

EXAMPLE 2

An Aα-isomer of fenvalerate was crystallized as in Example 1 except that 8.4% ammonia in methanol was not added. The resulting crystal was filtered to give 13.75 g of an Aα-isomer of fenvalerate having an Aα/Aβ ratio of 98.1/1.9.

EXAMPLE 3

Forty grams of a crystal of A-isomer of fenvalerate having an Aα/Aβ ratio of 46.9/53.1 was dissolved in 80 g of methanol under heating. The resulting solution was cooled to −16° C. and seeded with 1 mg of the crystal of Aα-isomer of fenvalerate prepared in Reference Example 1, and at the same time, 4.8 cc of 8.4% ammonia in methanol was added. The mixture was stirred at −16° C., and one day later, 1.4 cc of acetic acid was added to the mixture which was then filtered to give 33.56 g of a crystal of Aα-isomer of fenvalerate having an Aα/Aβ ratio of 96.8/3.2.

EXAMPLE 4

Five grams of the crystal of Aα-isomer of fenvalerate used in Comparative Example 1 was dissolved in 58.5 g of heptane and 6.5 g of toluene under heating, and the solution was cooled to 21° C. One mg of the crystal of Aα-isomer of fenvalerate prepared in Reference Example 1 was added to the solution which was then stirred for 2 hours, whereupon an Aα-isomer of fenvalerate was crystallized.

Individually, 50 g of the crystal of A-isomer of fenvalerate used in Example 1 was dissolved in 35 g of methanol under heating, and the solution was cooled to −17° C. To the cooled solution was added as a seed crystal all the crystal of Aα-isomer of fenvalerate prepared as above together with the mother liquor (the whole was in a slurry state), then 9 cc of 8.4% ammonia in methanol was added, and the resulting mixture was stirred for one day at −15.5° C. After addition of 3 cc of acetic acid, the mixture was filtered to give 31.05 g of a crystal of Aα-isomer of fenvalerate having an Aα/Aβ ratio of 96.8/3.2.

EXAMPLE 5

The crystal of Aα-isomer of fenvalerate (2.5 g) used in Comparative Example 1 was dissolved in 50 g of methanol under heating, and the solution was cooled to between 0° to 5° C. Thereafter, 1 mg of a crystal of Aα-isomer of fenvalerate (Aα/Aβ=99.8/0.2) was added to the solution which was then stirred for one hour and cooled to −15° C., whereupon an Aα-isomer of fenvalerate was crystallized, which mixture was in a slurry state as a whole.

Forty grams of the crystals of A-isomer of fenvalerate used in Example 1 was dissolved in 162.5 g of methanol under heating, and the solution was cooled to 26° C. The cooled solution was added to the slurry mixture prepared as above, and then 2.52 g of 12.9 g ammonia in methanol was added. The resulting mixture was stirred for two days at −15° C. After addition of 1.38 g of acetic acid, the mixture was filtered to give 28.68 g of a crystal of Aα-isomer of fenvalerate having an Aα/Aβ ratio of 98.2/1.8.

EXAMPLE 6

Five grams of the crystal of Aα-isomer of fenvalerate used in Comparative Example 1 was dissolved in 100 g of methanol under heating, and the solution was colled to between 0° to 5° C. After adding 1 mg of a crystal of Aα-isomer of fenvalerate (Aα/Aβ=99.8/0.2), the mixture was stirred for one hour and then cooled to −15° C., whereupon an Aα-isomer of fenvalerate was crystallized, which mixture was in a slurry state as a whole.

Individually, 50 g of the crystal of A-isomer of fenvalerate used in Example 1 was dissolved in 100 g of n-heptane under heating. The solution was cooled to 60° C., mixed with 75 g of methanol, and cooled to 25° C. The cooled solution was added to the slurry mixture prepared as above, and after addition of 3.14 g of 12.9% ammonia in methanol, the mixture was stirred for one day at −15° C. Following addition of 1.71 g of acetic acid, the mixture was filtered to give 28.32 g of a crystal of Aα-isomer of fenvalerate having an Aα/Aβ ratio of 98.6/1.4.

EXAMPLE 7

Five grams of the crystal of Aα-isomer of fenvalerate used in Comparative Example 1 was dissolved in 50 g of methanol under heating, and the solution was cooled to 20° C. After addition of 1 mg of a crystal of Aα-isomer of fenvalerate (Aα/Aβ=99.8/0.2), the mixture was stirred for one hour and then cooled to −15° C., whereupon an Aα-isomer of fenvalerate was crystallized, which mixture was in a slurry state as a whole.

Individually, 20 g of the crystal of A-isomer of fenvalerate used in Example 1 was dissolved in 200 g of methanol under heating, and the solution was cooled to 33° C. The cooled solution was added to the slurry mixture prepared as above, and after addition of 1.26 g of 12.9% ammonia in methanol, the mixture was stirred for two days at −15° C. Following addition of 0.69 g of acetic acid, the mixture was filtered to give 12.71 g of a crystal of Aα-isomer of fenvalerate having an Aα/Aβ ratio of 98.6/1.4.

REFERENCE EXAMPLE 2

Using a solution of a liquid A-isomer of fenvalerate (Aα/Aβ=46.9/53.1) in methanol, the region of a temperature versus concentration of A-isomer of fenvalerate profile where the supersaturated state of the solution could be maintained stably was determined by the method described below. The result is depicted by the graph of FIG. 2.

Figure 2:
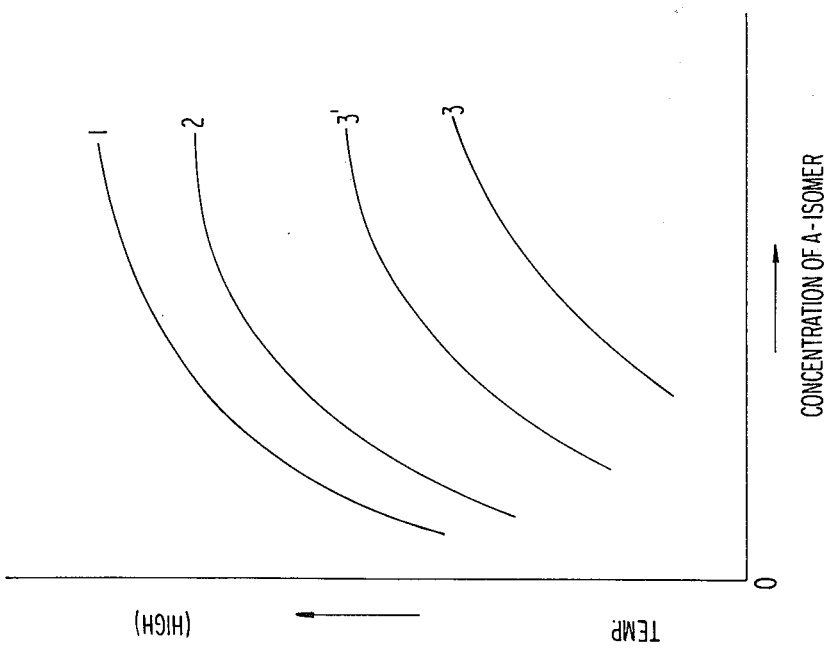
FIG. 2 is a schematic representation of the region of a temperature versus concentration of A-isomer profile for a methanol solution of the A-isomer of fenvalerate as determined by the method described in Reference Example 2.

The solubility in methanol of crystallized A-isomer of fenvalerate obtained by crystallizing the A-isomer described above, that was used in Example 3, was determined, and the result is depicted by curve ①  in FIG. 2. Then, a solution of a certain concentration of A-isomer of fenvalerate in methanol was heated under reflux condition and then cooled to a predetermined temperature, and to the solution was added the crystal of Aα-isomer of fenvalerate obtained in Reference Example 1, and the mixture was checked whether the dissolution of the crystal tool place at that temperature. The result is depicted by curve ②  . Ten mg of ferric oxide was added to 300 cc of a solution of a certain concentration of A-isomer of fenvalerate in methanol as a substance to upset the supersaturated state of the solution. After heating the solution under reflux condition, then cooling to a predetermined temperature and holding it at that temperature for 24 hours, the solution was checked whether the crystallization of the A-isomer of fenvalerate took place. The result is depicted by curve ③  . Three hundred cc of a solution of certain concentration of A-isomer of fenvalerate in methanol was heated under reflux condition and then cooled to a predetermined temperature, and 10 mg of ferric oxide was added to the solution which was left to stand for 24 hours and checked whether the crystallization of the A-isomer of fenvalerate took place. The result is depicted by curve ③ '.

COMPARATIVE EXAMPLE 4

A hundred grams of the A-isomer of fenvalerate used in Example 3 was mixed with 100 g of methanol and 10 mg of iron rust, and the mixture was heated under reflux condition for 30 minutes. The mixture was cooled to −5° C. at which it was stirred for about 7 hours. Then, a large amount of crystal was obtained. Analysis of a part of it showed that it was a crystal of A-isomer of fenvalerate having an Aα/Aβ ratio of 46.5/53.5.

COMPARATIVE EXAMPLE 5

A hundred grams of the A-isomer of fenvalerate used in Example 3 was mixed with 117 g of n-heptane, 13 g of toluene and 70 g of methanol, and the mixture was heated under reflux condition for 30 minutes. The resulting mixture was cooled to $-15°$ C. and it was held at that temperature under stirring. When 5 mg of iron rust was added to the mixture, a large amount of crystal was obtained about 5 hours later. Analysis of a part of it showed that it was a crystal of A-isomer of fenvalerate having an $A\alpha/A\beta$ ratio of 46.0/54.0. The crystal was further heated under reflux condition for an additional 30 minutes, cooled to $-15°$ C. and held at that temperature under stirring. About 8 hours later, a large amount of crystal was produced, and it was found to be a crystal of A-isomer of fenvalerate having an $A\alpha/A\beta$ ratio of 45.8/54.2.

COMPARATIVE EXAMPLE 6

A hundred grams of the A-isomer of fenvalerate used in Example 3 was mixed with 200 g of methanol and 10 mg of iron rust, and the mixture was heated under reflux condition for 30 minutes. The resulting mixture was cooled to $-15°$ C. and held at that temperature under stirring.

Individually, 10 g of a crystal of $A\alpha$-isomer of fenvalerate having an $A\alpha/A\beta$ ratio of 97.6/2.4 was mixed with 27 g of n-heptane and 3 g of toluene, and the mixture was heated under reflux condition for 30 minutes, followed by cooling to 35° C. At that temperature, the mixture was further mixed with 1 mg of the crystal of $A\alpha$-isomer of fenvalerate as described above and stirred for 30 minutes. It was then cooled to 30° C. and held at that temperature for one hour under stirring, whereupon a crystal of $A\alpha$-isomer of fenvalerate was formed. To the solution of A-isomer of fenvalerate that had been held at $-15°$ C. under stirring was added as a seed crystal all the crystal of $A\alpha$-isomer of fenvalerate prepared as above together with the mother liquor at $-15°$ C. (the whole was in a slurry state), and at the same time, 6.29 g of 12.9% ammonia in methanol was added, and the resulting mixture was stirred for 24 hours at $-15°$ C. Acetic acid (3.43 g) was added to the mixture which was then filtered to give 103.7 g of a crystal of A-isomer of fenvalerate having an $A\alpha/A\beta$ ratio of 45.1/54.9.

COMPARATIVE EXAMPLE 7

Forty grams of the crystal of A-isomer of fenvalerate used in Example 3 and 10 mg of iron rust were mixed with 80 g of methanol under heating, and the solution was cooled to $-16°$ C. The solution was seeded with 1 mg of the crystal of $A\alpha$-isomer of fenvalerate obtained in Reference Example 1, and at the same time, 4.8 cc of 8.4% ammonia in methanol was added thereto. The resulting solution was stirred at $-16°$ C., and one day later, 1.4 cc of acetic acid was added to the solution which was then filtered to give 38.07 g of a crystal of A-isomer of fenvalerate having an $A\alpha/A\beta$ ratio of 44.5/55.5.

EXAMPLE 8

A hundred grams of a liquid A-isomer of fenvalerate having an $A\alpha/A\beta$ ratio of 46.9/53.1 was mixed with 200 g of methanol together with 10 mg of iron rust and 10 glass beads of about 1 mm in diameter used as substances to upset the supersaturated state of the solution. The solution was heated under reflux condition for 30 minutes and cooled to 5° C. The resulting solution was stirred for 24 hours at that temperature, and no crystal of A-isomer of fenvalerate was formed.

Three grams of a crystal of $A\alpha$-isomer of fenvalerate having an $A\alpha/A\beta$ ratio of 98.0/2.0 was mixed with 8.1 g of n-heptane and 0.9 g of toluene. The solution was heated under reflux condition for 30 minutes and cooled to 35° C. At that temperature, 1 mg of the crystal of $A\alpha$-isomer of fenvalerate as described above was added to the solution which was stirred for an additional 30 minutes. Then, the solution was cooled to 30° C. and held at that temperature for one hour under stirring, whereupon a crystal of $A\alpha$-isomer of fenvalerate was obtained. To the solution of A-isomer of fenvalerate that had been held at 5° C. under stirring was added all the crystal of $A\alpha$-isomer of fenvalerate thus-obtained as a seed crystal together with the mother liquor, and at the same time, 2.41 g of triethylamine was added thereto. The resulting mixture was stirred for 25 hours at 5° C., and then, 2.98 g of 35% hydrochloric acid was added to the mixture which was filtered to give 54.39 g of a crystal of $A\alpha$-isomer of fenvalerate having an $A\alpha/A\beta$ ratio of 98.6/1.4.

EXAMPLE 9

The A-isomer of fenvalerate (79.6 g) used in Example 8 was mixed with 185.7 g of methanol together with 10 mg of ferric oxide. The solution was heated under reflux condition for 30 minutes and cooled to 15° C. The resulting solution was stirred for 24 hours at that temperature, and no crystal of A-isomer of fenvalerate was formed.

Individually, a crystal of $A\alpha$-isomer of fenvalerate (3.98 g) having an $A\alpha/A\beta$ ratio of 99.9/0.1 was dissolved in 10.75 g of n-heptane and 1.19 g of toluene, and the solution was heated under reflux condition for 30 minutes. The resulting solution was cooled to 35° C., and at that temperature, 1 mg of the crystal of $A\alpha$-isomer of fenvalerate as described above was added to the solution which was stirred for an additional 30 minutes. Then, it was cooled to 30° C. and held at that temperature for one hour under stirring, whereupon a crystal of $A\alpha$-isomer of fenvalerate was formed. To the solution of A-isomer of fenvalerate that had been held at 15° C. under stirring was added all the crystal of $A\alpha$-isomer of fenvalerate thus-formed as a seed crystal together with the mother liquor, and at the same time, 1.92 g of triethylamine was added, and the resulting mixture was stirred for 20 hours at 15° C., whereupon a crystal of $A\alpha$-isomer of fenvalerate was formed. Then, the reaction mixture was cooled gradually to 10° C. at which temperature it was stirred for 24 hours, and further cooled to 5° C. at which temperature it was stirred for 4 hours. Then, 2.96 g of 35% hydrochloric acid was added to the mixture, which was then filtered to give 28.18 g of a crystal of $A\alpha$-isomer of fenvalerate having an $A\alpha/A\beta$ ratio of 98.3/1.7.

EXAMPLE 10

The A-isomer of fenvalerate (150.0 g) used in Example 8 was mixed with 850.0 g of methanol together with 50 mg of ferric oxide. The solution was heated under reflux condition for 30 minutes and cooled to 0° C.

Individually, a crystal of $A\alpha$-isomer of fenvalerate (7.50 g) having an $A\alpha/A\beta$ ratio of 99.0/1.0 was dissolved in 20.25 g of n-heptane and 2.25 g of toluene, and the solution was heated under reflux condition for 30 minutes and cooled to 35° C. At that temerature, 1 mg of the crystal of Aα-isomer of fenvalerate as described above was added to the solution which was stirred for 30 minutes. Then, it was cooled to 30° C. and held at that temperature for one hour under stirring, whereupon a crystal of Aα-isomer of fenvalerate was formed.

To the solution of A-isomer that had been held at 0° C. was added all the crystal of Aα-isomer of fenvalerate thus-formed as a seed crystal together with the mother liquor, and the resulting mixture was held at 0° C. for 24 hours under stirring. By filtering the mixture, 37.57 g of a crystal of Aα-isomer of fenvalerate having an Aα/Aβ ratio of 99.2/0.8 was obtained.

EXAMPLE 11

Sixty grams of the A-isomer of fenvalerate used in Example 8 was dissolved in 240.0 g of methanol, and the solution was heated under reflux condition for 30 minutes, followed by cooling to 10° C.

Individually, 10 g of a crystal of Aα-isomer of fenvalerate having an Aα/Aβ ratio of 99.9/0.1 was mixed with 12.0 g of methanol and 0.06 g of acetic acid. The mixture was heated under reflux condition for 30 minutes and cooled to 30° C. At that temperature, 1 mg of the crystal of Aα-isomer of fenvalerate as described above was added to the mixture which was stirred for one hour, whereupon a crystal of Aα-isomer of fenvalerate was formed.

To the solution of A-isomer of fenvalerate that had been held at 10° C. was added all the crystal of Aα-isomer of fenvalerate thus-formed as a seed crystal together with the mother liquor, and the resulting mixture was held at 10° C. for 24 hours under stirring. By filtering the mixture, 9.62 g of a crystal of Aα-isomer of fenvalerate having an Aα/Aβ ratio of 99.0/1.0 was obtained.

EXAMPLE 12

Sixty grams of the A-isomer of fenvalerate used in Example 8 was dissolved in 240.0 g of methanol and 1.2 g of acetic acid, and the solution was heated under reflux condition for 30 minutes and then cooled to 10° C.

Individually, 10 g of a crystal of Aα-isomer of fenvalerate having an Aα/Aβ ratio of 98.3/1.7 was dissolved in 27.0 g of n-heptane and 3.0 g of toluene, and the solution was heated under reflux condition for 30 minutes and then cooled to 35° C. At that temperature, 1 mg of the crystal of Aα-isomer of fenvalerate as described above was added to the solution which was stirred for 30 minutes. Then, it was cooled to 30° C. and held at that temperature for one hour under stirring, whereupon a crystal of Aα-isomer of fenvalerate was formed.

To the solution of A-isomer of fenvalerate that had been held at 10° C. under stirring was added about 1 cc of the slurry of the crystal of Aα-isomer of fenvalerate thus-formed as a need crystal, and the resulting mixture was held at 10° C. for 20 hours under stirring. The mixture was then filtered to give 8.84 g of a crystal of Aα-isomer of fenvalerate having an Aα/Aβ ratio of 99.7/0.3.

While the invention has been described in detail and with reference to specific embodiments thereof, it will be apparent to one skilled in the art that various changes and modifications can be made therein without departing from the spirit and scope thereof.

What is claimed is:

1. A method for preparing an optically active carboxylic acid ester of the formula (I):

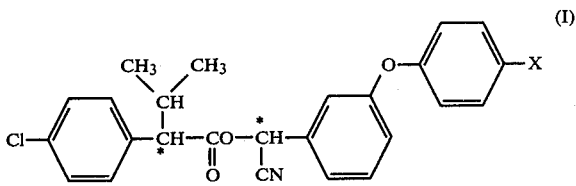

wherein X is a hydrogen atom or a fluorine atom, and
* indicates an asymmetric carbon atom, which is an Aα-isomer having an (S)-configuration on both the acid and alcohol moieties, or rich in said Aα-isomer, which method comprises crystallizing said Aα-isomer from a solution of an A-isomer of the compound of formula (I) having an (S)-configuration on the acid moiety in the presence of a crystal of substantially pure Aα-isomer and in the absence of any crystal of the A-isomer and in the presence or absence of a basic catalyst, wherein the solution of the A-isomer is heated to a temperature of 40° C. or higher before the Aα-isomer is crystallized from that solution.

2. A method according to claim 1, wherein the Aα-isomer is crystallized from a supersaturated solution of the A-isomer that is in the region of a temperature versus concentration of A-isomer profile where no additional amount of Aα-isomer is dissolved and the supersaturated state of the solution is maintained stably, in the presence of a crystal that is of substantially pure Aα-isomer as a seed crystal.

3. A method according to claim 1, wherein the seed crystal is a crystal of Aα-isomer that is obtained by recrystallization.

4. A method according to claim 2, wherein the seed crystal is a crystal of Aα-isomer that is obtained by recrystallization.

5. A method according to claim 4, wherein the Aα-isomer is crystallized in a solvent, and the thus-obtained crystal is not isolated but is mixed with the solution of A-isomer as a seed crystal together with the mother liquor.

6. A method according to claim 3, wherein the Aα-isomer is recrystallized in a solvent, and the thus-obtained crystal is not isolated but is mixed with the solution of A-isomer as a seed crystal together with the mother liquor.

7. A method according to any of claims 3, 4 and 5, 6, wherein the seed crystal is obtained by recrystallization from a solvent which is made of one or more solvents selected from alcohols, aliphatic hydrocarbons and alicyclic hydrocarbons, or a solvent containing one or more of these solvents.

8. A method according to any of claims 3, 4 and 5, 6, wherein the seed crystal is obtained by recrystallization from a solvent which is made of one or more solvents selected from alcohols, aliphatic hydrocarbons and alicyclic hydrocarbons, or a solvent containing one or more of these solvents, said solvent containing not more than 5 wt% of acetic acid on the basis of the total amount of the solvent used.

9. A method according to any of claims 3, 4 and 5, 6, wherein the seed crystal is obtained by recrystallization from a solvent which is made of a mixture of an aromatic hydrocarbon with one or more solvents selected from alcohols, aliphatic hydrocarbons and alicyclic hydrocarbons.

10. A method according to any of claims 3, 4 and 5, 6, wherein the seed crystal is obtained by recrystallization from a solvent which is made of a mixture of an aromatic hydrocarbon with one or more solvents selected from alcohols, aliphatic hydrocarbons and alicyclic hydrocarbons, said solvent containing not more than 5 wt% of acetic acid on the basis of the total amount of the solvent used.

11. A method according to claim 7, wherein the recrystallization solvent is used in a weight of from 0.5 to 50 times as great as that of the A$\alpha$-isomer used.

12. A method according to claim 8, wherein the recrystallization solvent is used in a weight of from 0.5 to 50 times as great as that of the A$\alpha$-isomer used.

13. A method according to claim 9, wherein the recrystallization solvent is used in a weight of from 0.5 to 50 times as great as that of the A$\alpha$-isomer used.

14. A method according to claim 10, wherein the recrystallization solvent is used in a weight of from 0.5 to 50 times as great as that of the A$\alpha$-isomer used.

15. A method according to any of claims 2, 3, 4, 5 and 6, wherein the A$\alpha$-isomer is crystallized from the solution of A-isomer using a solvent made of one or more solvents selected from alcohols, aliphatic hydrocarbons and alicyclic hydrocarbons, or a solvent containing one or more of these solvents.

16. A method according to any of claims 1, 2, 3, 4, 5 and 6, wherein the A$\alpha$-isomer is crystallized from the solution of A-isomer in the absence of a basic catalyst using a solvent made of one or more solvents selected from alcohols, aliphatic hydrocarbons and alicyclic hydrocarbons, or a solvent containing one or more of these solvents, said solvent containing not more than 5 wt% of acetic acid on the basis of the total amount of the solvent used.

17. A method according to any of claims 1, 2, 3, 4, 5 and 6, wherein the A$\alpha$-isomer is crystallized from the solution of A-isomer using an alcohol as the solvent.

18. A method according to any of claims 1, 2, 3, 4, 5 and 6, wherein the A$\alpha$-isomer is crystallized from the solution of A-isomer in the absence of a basic catalyst using an alcohol as the solvent that contains not more than 5 wt% of acetic acid on the basis of the total amount of the solvent used.

19. A method according to any of claims 1, 2, 3, 4, 5 and 6, wherein the A$\alpha$-isomer is crystallized from the solution of A-isomer using a solvent made of a mixture of an alcohol with one or more solvents selected from aliphatic hydrocarbons, alicyclic hydrocarbons and aromatic hydrocarbons.

20. A method according to any of claims 1, 2, 3, 4, 5 and 6, wherein the A$\alpha$-isomer is crystallized from the solution of A-isomer in the absence of a basic catalyst using a solvent made of a mixture of an alcohol with one or more solvents selected from aliphatic hydrocarbons, alicyclic hydrocarbons and aromatic hydrocarbons, said solvent containing not more than 5 wt% of acetic acid on the basis of the total amount of the solvents used.

21. A method according to any of claims 1, 2, 3, 4, 5 and 6, wherein the A$\alpha$-isomer is crystallized in the presence of a basic catalyst.

22. A method according to claim 21, wherein the basic catalyst is ammonia or triethylamine.

23. A method according to claim 15, wherein the A$\alpha$-isomer is crystallized in the presence of a basic catalyst.

24. A method according to claim 23, wherein the basic catalyst is ammonia or triethylamine.

25. A method according to claim 17, wherein the A$\alpha$-isomer is crystallized in the presence of a basic catalyst.

26. A method according to claim 25, wherein the basic catalyst is ammonia or triethylamine.

27. A method according to claim 19, wherein the A$\alpha$-isomer is crystallized in the presence of a basic catalyst.

28. A method according to claim 27, wherein the basic catalyst is ammonia or triethylamine.

29. A method according to claims 1, 2, 3, 4, 5 and 6, wherein the A$\alpha$-isomer is crystallized in the presence of a basic catalyst, and the crystal of A$\alpha$-isomer is recovered together with the A-isomer in the mother liquor to obtain an A-isomer rich in the A$\alpha$-isomer.

30. A method according to claim 29, wherein the basic catalyst is ammonia or triethylamine.

31. A method according to claim 15, wherein the A$\alpha$-isomer is crystallized in the presence of a basic catalyst, and the crystal of A$\alpha$-isomer is recovered together with the A-isomer is the mother liquor to obtain an A-isomer rich in the A$\alpha$-isomer.

32. A method according to claim 31, wherein the basic catalyst is ammonia or triethylamine.

33. A method according to claim 17, wherein the A$\alpha$-isomer is crystallized in the presence of a basic catalyst, and the crystal of A$\alpha$-isomer is recovered together with the A-isomer in the mother liquor to obtain an A-isomer rich in the A$\alpha$-isomer.

34. A method according to claim 33, wherein the basic catalyst is ammonia or triethylamine.

35. A method according to claim 19, wherein the A$\alpha$-isomer is crystallized in the presence of a basic catalyst, and the crystal of A$\alpha$-isomer is recovered together with the A-isomer in the mother liquor to obtain an A-isomer rich in the A$\alpha$-isomer.

36. A method according to claim 35, wherein the basic catalyst is ammonia or triethylamine.

37. A method according in any of claims 1, 2, 3, 4, 5 and 6, wherein the substituent X in the carboxylic acid ester of the formula (I) is a hydrogen atom.

38. A method according to claim 15, wherein the substitutent X in the carboxylic acid ester of the formula (1) is a hydrogen atom.

39. A method according to claim 16, wherein the substituent X in the carboxylic acid ester of the formula (I) is a hydrogen atom.

40. A method according to claim 17, wherein the substituent X in the carboxylic acid ester of the formula (I) is a hydrogen atom.

41. A method according to claim 18, wherein the substituent X in the carboxylic acid ester of the formula (I) is a hydrogen atom.

42. A method according to claim 19, wherein the substituent X in the carboxylic acid ester of the formula (I) is a hydrogen atom.

43. A method according to claim 20, wherein the substituent X in the carboxylic acid ester of the formula (I) is a hydrogen atom.

44. A method according to claim 21, wherein the substituent X in the carboxylic acid ester of the formula (I) is a hydrogen atom.

45. A method according to claim 22, wherein the substituent X in the carboxylic acid ester of the formula (I) is a hydrogen atom.

46. A method according to claim 23, wherein the substituent X in the carboxylic acid ester of the formula (I) is a hydrogen atom.

47. A method according to claim 24, wherein the substituent X in the carboxylic acid ester of the formula (I) is a hydrogen atom.

48. A method according to claim 25, wherein the substituent X in the carboxylic acid ester of the formula (I) is a hydrogen atom.

49. A method according to claim 26, wherein the substituent X in the carboxylic acid ester of the formula (I) is a hydrogen atom.

50. A method according to claim 27, wherein the substituent X in the carboxylic acid ester of the formula (I) is a hydrogen atom.

51. A method according to claim 28, wherein the substituent X in the carboxylic acid ester of the formula (I) is a hydrogen atom.

52. A method according to claim 29, wherein the substituent X in the carboxylic acid ester of the formula (I) is a hydrogen atom.

53. A method according to claim 30, wherein the substituent X in the carboxylic acid ester of the formula (I) is a hydrogen atom.

54. A method according to claim 31, wherein the substituent X in the carboxylic acid ester of the formula (I) is a hydrogen atom.

55. A method according to claim 32, wherein the substituent X in the carboxylic acid ester of the formula (I) is a hydrogen atom.

56. A method according to claim 33, wherein the substituent X in the carboxylic acid ester of the formula (I) is a hydrogen atom.

57. A method according to claim 34, wherein the substituent X in the carboxylic acid ester of the formula (I) is a hydrogen atom.

58. A method according to claim 35, wherein the substituent X in the carboxylic acid ester of the formula (I) is a hydrogen atom.

59. A method according to claim 36, wherein the substituent X in the carboxylic acid ester of the formula (I) is a hydrogen atom.

* * * * *